United States Patent [19]

Nakashio et al.

[11] 3,972,997

[45] Aug. 3, 1976

[54] NOVEL COSMETICS CONTAINING PULLULAN

[75] Inventors: Seizo Nakashio, Nishinomiya; Kozo Tsuji; Nobuhiro Toyota, both of Osaka; Fumio Fujita, Osaka, all of Japan

[73] Assignees: Sumitomo Chemical Company, Limited, Osaka; Hayashibara Biochemical Laboratories, Incorporated, Okayama, both of Japan

[22] Filed: Oct. 3, 1974

[21] Appl. No.: 511,524

[30] Foreign Application Priority Data
Oct. 16, 1973 Japan.............................. 48-116652

[52] U.S. Cl................................... 424/49; 424/69; 424/70; 424/71; 424/181; 424/283
[51] Int. Cl.$^2$......................................... A61K 7/16
[58] Field of Search .................. 424/49, 50, 69, 70, 424/283

[56] References Cited
UNITED STATES PATENTS
3,827,937   8/1974   Kato et al.......................... 195/31 P

OTHER PUBLICATIONS

Sagarin – "Cosmetics–Science & Technology" pp. 167–168 1957.
Chemical Abstracts 76:90.010z (1972).

Primary Examiner—Leonard Schenkman
Attorney, Agent, or Firm—Stevens, Davis, Miller & Mosher

[57] ABSTRACT

A cosmetic can be improved and enhanced in its effect when incorporated with pullulan, which is a linear high polymer having repetition units, bonded through α-1,6-linkages, of maltotriose, a trimer of glucose, and is represented by the formula,

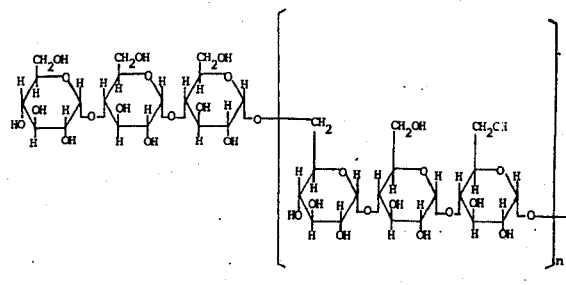

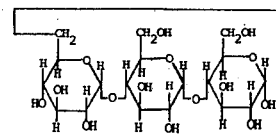

wherein $n$ represents the polymerization degree and is an integer of 10 to 10,000.

2 Claims, No Drawings

NOVEL COSMETICS CONTAINING PULLULAN

This invention relates to a cosmetic containing pullulan. More particularly, the invention pertains to a cosmetic in which pullulan is used, taking advantage of its excellent transparent film-forming ability, moisture absorptivity, water solubility, tackiness, dispersibility and non-toxicity.

The pullulan is a linear high polymer having repetition units, bonded throgh α-1,6-linkages, of maltotriose, a trimer of glucose, and has a molecular structure represented by the formula,

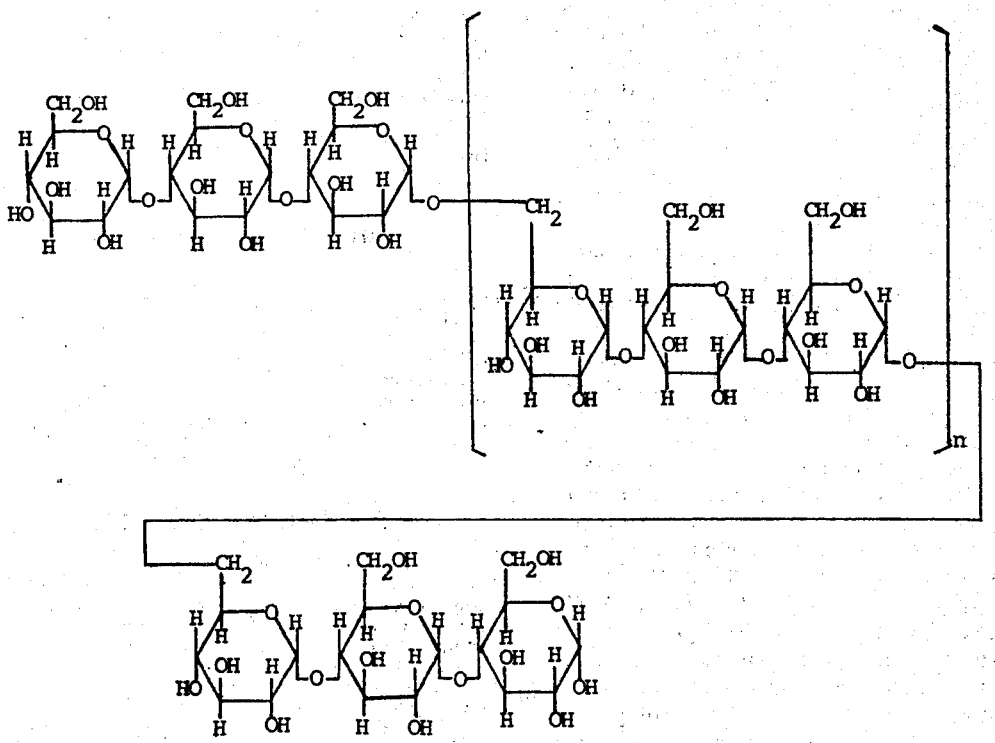

wherein $n$ represents the polymerization degree and is an integer of 10 to 10,000.

The pullulan has heretofore been known merely as a water-soluble tacky substance, and is a novel substance which is unknown in the field of cosmetics.

In the field of cosmetics, there have conventionally been used high polymers which are water-soluble like the pullulan. However, the pullulan used in the present invention, despite of its glucose units containing in the molecule, is entirely different in molecular structure from polysaccharides, or derivatives thereof, such as starch, tragacanth gum, methyl cellulose, carboxymethyl cellulose, hydroxyethyl cellulose and sodium alginate which also are glucose derivatives having glucose units and have been used as cosmetics hitherto. Furthermore, the pullulan is markedly different in properties from said polysaccharides. For example, it is easily soluble in cold water, and its aqueous solution is stable over a long period of time and brings about no gelation nor so-called "aging" phenomenon. This is a characteristic which is greatly different from the properties of starches. In addition, the pullulan is characteristically lower in aqueous solution viscosity than any of such high polymers for cosmetic as mentioned above, even when the two are same in solute concentration or molecular weight.

The pullulan is substantially non-crystalline, when viewed from its crystal structure, and forms a film which is excellent in transparency and gloss and which can maintain its transparency over a long period of time. The pullulan is high in film-forming ability, and gives a film excellent in strength. In this respect, the pullulan is superior to the aforesaid high polymers. Further, the pullulan is not only high in tackiness and adhesion but also has such high dispersion stability as to form a protective collid. This is a great characteristic which differs considerably from the characteristics of the aforesaid high polymers. In addition, the pullulan is non-toxic and non-irritant to human body and has such features as being tasteless and odorless.

Because of such characteristic features as mentioned above, the pullulan may be applied to any cosmetics, but is preferably used as an ingredient of cosmetic lotions, cosmetic powders, rouges, cosmetic around the eyes, facial packs, shampoos, specific hair dressings (set lotions and hair lacquers), and tooth powders. That is, the pullulan can be used as a tacky ingredient of cosmetic lotions, taking advantage not only of its higher viscosity but also of its solution stability, non-toxicity and transparent film-forming ability; as an ingredient of cosmetic powders (including solid cosmetics), taking advantage of its covering power, adsorptivity and tackiness; as an ingredient of rouges, e.g. liquid rouges and paste rouges, taking advantage of its odorlessness, tastelessness, non-toxicity, high water solubility and tackiness; as an ingredient of cosmetics around the eyes, e.g. eye liners, taking advantage of its non-toxicity, non-irritability and film-forming ability; as an ingredient of facial packs, taking advantage of its superiority to polyvinyl alcohols, which have heretofore been used relatively frequently, in film-forming ability, adsorptivity, water retainability, continuity of film at the time of peeling, and ability of giving tension to the skin due to shrinkage of film at the time of drying; as an ingredient of shampoos, taking advantage of its foaming-promoting effect and builder effect; as an ingredient of set lotions and hair lacquers, taking advantage of its takiness, ability of forming tough film, hair setting ability, and high water solubility necessary for removal after use; as an ingredient of tooth paste, taking advantage of its excellent coherence (protective colloid-forming ability), foamability, high viscosity, non-toxicity and storage stability.

In preparing cosmetics according to the present invention, the pullulan may be freely used, without any particular limitation, in combination with other high polymers, low molecular weight compounds, inorganic compounds, perfumes, preservatives, etc. which are used at the time of preparation of the cosmetics, any may be used in cosmetics of any composition. As to the materials to be used for preparation of cosmetics, reference may be made to many examples, literatures and reports such as, for example, "Keshohin-gaku (Cosmetics)" edited by Tessaku Ikeda (published by Nanzan-do).

The content of the pullulan in a cosmetic is variable depending on the kind of the cosmetic, but is ordinarily from 0.01 to 99 parts by weight per 100 parts by weight of the total cosmetic.

The pullulan used in the present invention is not particularly restricted in production process, and may be produced by biochemical synthesis process (e.g. U.S. Pat. No. 3,827,937). At present, however, it is obtained as a tacky substance secreted in the culture liquor of a strain of the genus pullularia which is an incomplete microorganism. for example, a strain pullularia pullulans is subjected to shaking culture at 24°C for 5 days in a medium containing 10 % of partially hydrolyzed starch, 0.5 % of $K_2HPO_4$, 0.1 % of NaCl, 0.02 % of $MgSO_4·7H_2O$, 0.06 % of $(NH_4)_2SO_4$ and 0.04 % of yeast extract, whereby the pullulans is obtained as a tacky substance in the culture liquor. If necessary, the culture liquor is freed from the cells by centrifugation, and the supernatant is charged with methanol to from a pullulan precipitate, which is then separated, repeatedly subjected to water-dissolution and methanol precipitation, and thereafter dried, whereby purified pullulan is obtained in a yield of 60 to 70 % based on the saccharide. The pullulan somewhat varies in physical properties depending on the kind of the strain from which it is produced, though this is not greatly concerned with the efficiency thereof as a cosmetic.

The molecular weight of the pullulan used in the present invention is not particularly limited, but is preferably in the range from 5,000 to 5,000,000.

Prescription examples of the novel cosmetics of the present invention are shown below, but the invention is not limited to the examples.

PRESCRIPTION EXAMPLE 1

| Cosmetic lotion: | |
|---|---|
| Ethyl alcohol | 10.0 parts (weight) |
| Pullulan (molecular weight 400,000) | 0.05 parts (weight) |
| Propylene glycol | 5.0 parts (weight) |
| Oleyl alcohol | 0.1 parts (weight) |
| Polyoxyethylene sorbitan monolaurate | 1.2 parts (weight) |
| Perfume | 0.2 parts (weight) |
| Purified water | 83.45 parts (weight) |
| Antioxidant and antiseptic | Proper amounts |

PRESCRIPTION EXAMPLE 2

| Cosmetic powder: | |
|---|---|
| Talc | 80.0 parts (weight) |
| Zinc white | 4.5 parts (weight) |
| Zinc stearate | 4.5 parts (weight) |
| Pullulan (molecular weight 10,000) | 11.0 parts (weight) |
| Perfume | Proper amount |
| Dye | Proper amount |

PRESCRIPTION EXAMPLE 3

| Cosmetic powder: | |
|---|---|
| Titanium white | 78 parts (weight) |
| Mineral oil | 8 parts (weight) |
| Pullulan (molecular weight 100,000) | 8 parts (weight) |
| Purified water | 6 parts (weight) |
| Perfume | Proper amount |
| Dye | Proper amount |

PRESCRIPTION EXAMPLE 4

| Rouge: | |
|---|---|
| Purified water | 98 parts (weight) |
| Pullulan (molecular weight 400,000) | 2 parts (weight) |
| Wetting agent | 0.1 - 0.2 parts (weight) |
| Water-soluble dye | Proper amount |
| Perfume | Proper amount |
| Antiseptic | Proper amount |

PRESCRIPTION EXAMPLE 5

| Cosmetic around the eyes: | |
|---|---|
| Cetyl alcohol sulfuric ester | 1.8 parts (weight) |
| Sorbitan monooleate | 0.4 parts (weight) |
| Propylene glycol | 6.5 parts (weight) |
| Pullulan (molecular weight 400,000) | 2.5 parts (weight) |
| Ethyl alcohol | 9.0 parts (weight) |
| Purified water | 79.8 parts (weight) |
| Antiseptic | Proper amount |
| Pigment | Proper amount |

PRESCRIPTION EXAMPLE 6

| Facial pack: | |
|---|---|
| Pullulan (molecular weight 150,000) | 20 parts (weight) |
| Carboxymethyl cellulose | 5 parts (weight) |
| Glycerin | 2 parts (weight) |
| Ethyl alcohol | 5 parts (weight) |
| Purified water | 65 parts (weight) |
| Perfume | Proper amount |
| Antiseptic | Proper amount |

PRESCRIPTION EXAMPLE 7

| Shampoo: | |
|---|---|
| Pullulan (molecular weight 800,000) | 2.0 parts (weight) |
| Ethyl alcohol | 13.0 parts (weight) |
| Glycerin | 2.0 parts (weight) |
| Purified water | 80.0 parts (weight) |
| Perfume | 0.3 parts (weight) |
| Polyoxyethylene sorbitan monolaurate | 1.5 parts (weight) |
| Antiseptic and antioxidant | Proper amounts |
| Coloring agent | Proper amount |

PRESCRIPTION EXAMPLE 8

Set Lotion:
| | |
|---|---|
| Pullulan (molecular weight 800,000) | 1.0 parts (weight) |
| Ethyl alcohol | 5.0 parts (weight) |
| Citric acid | 0.2 parts (weight) |
| Purified water | 93.0 parts (weight) |
| Polyoxyethylene sorbitan monooleate | 1.0 parts (weight) |
| Perfume | 0.2 parts (weight) |
| Antiseptic and antioxidant | Proper amounts |
| E.D.T.A. (ethylenediamine tetrasodium tetracetate) | 0.05 parts |
| Coloring agent | Proper amount |

PRESCRIPTION EXAMPLE 9

Tooth paste:
| | |
|---|---|
| Calcium diphosphate | 40.0 parts (weight) |
| Sodium metaphosphate | 4.0 parts (weight) |
| Pullulan (molecular weight 70,000) | 20.0 parts (weight) |
| Purified water | 20.0 parts (weight) |
| Glycerin | 5.0 parts (weight) |
| Sodium laurylsulfate | 2.0 parts (weight) |
| Saccharine | 0.05 parts (weight) |
| Perfume | 1.0 parts (weight) |
| Wetting agent | 1.0 parts (weight) |
| Dye | Proper amount |

What is claimed is:

1. A cosmetic containing pullulan having a molecular weight of 5,000 to 5,000,000 as an ingredient of cosmetic lotions, cosmetic powders, rouges, cosmetics for use around the eyes, facial packs, shampoos, set lotions, hari lacquers and tooth paste, the content of said pullulan being 0.01 to 99 parts by weight per 100 parts by weight of the total cosmetic.

2. A cosmetic according to claim 1, wherein the pullulan has a molecular weight of 10,000 to 800,000.

* * * * *